United States Patent [19]

Van der Knapp

[11] Patent Number: Plant 6,739

[45] Date of Patent: Apr. 18, 1989

[54] CHRYSANTHEMUM PLANT NAMED TOPPER

[75] Inventor: Jacques C. M. Van der Knapp, De Lier, Netherlands

[73] Assignee: Fides Beheer B.V., De Lier, Netherlands

[21] Appl. No.: 123,906

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum cultivar named Topper, having flat capitulum form and single capitulum type, and clear white ray florets. The disc florets are yellow-green when immature, maturing to yellow, with some green remaining in the center of the disc florets.

1 Drawing Sheet

The present invention comprises a new and distinct cultivar of *Chrysanthemum morifolium,* hereinafter referred to by the cultivar name Topper.

Topper is a product of a planned breeding program which had the objective of creating new Chrysanthemum cultivars with single capitulum type, clear white ray floret, nine (9) week response, and the ability to produce commercially acceptable quality in year around cut mum program. Such traits in combination were not present or needed improvement in previously available commercial cultivars.

Topper was originated from a hybridization made by applicant in a controlled breeding program in De Lier, Holland in 1980. The female parent was Canary, an unpatented and commercial cultivar. The male parent of Topper was Orca, unpatented and commercialized only in Holland.

Topper was discovered and selected as one flowering plant within the progeny of the stated parentage by Jacques C. M. Van der Knapp in August 1980 in a controlled environment in De Lier, Holland.

The first act of asexual reproduction of Topper was accomplished when vegetative cuttings were taken from the initial selection in October 1980 in a controlled environment in De Lier, Holland by a technician working under formulations established and supervised by Jacques C. M. Van der Knapp. Horticultural examination of selected units initiated in April 1981 has demonstrated that the combination of characteristics as herein disclosed for Topper are firmly fixed and are retained through successive generations of asexual reproduction.

Topper has not observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Topper, which in combination distinguish this Chrysanthemum as a new and distinct cultivar:

1. Flat capitulum form.
2. Single capitulum type.
3. Clear white ray floret.

4. Diameter across the face of the capitulum is 65–75 mm.
5. Green (immature) to primarily yellow (mature) disc florets. At maturity, the green center is reduced in size but still remains.

Of the many commercial cultivars known to the present inventor, the most similar in comparison to Topper is White Marble. In comparison to White Marble, Topper has a faster response, less compounding, better leaves, and more pollen in late stage of flowering. The capitulum form, capitulum type, and disc flower color are similar to those same characteristics of White Marble.

The accompanying photographic drawing shows in perspective view typical inflorescence and foliage characteristics of Topper, with colors being as nearly true as possible with illustrations of this type.

In the following description, color references are made to The Royal Horticultural Society Colour Chart. The color values were determined between 11:00–12:00 a.m. in October 1982 under natural daylight at De Lier, Holland.

Classification:

*Botanical.*—*Chrysanthemum morifolium,* Ramat., cv. Topper.

*Commercial.*—Cut daisy spray.

INFLORESCENCE

A. Capitulum

*Form.*—Flat.

*Type.*—Single.

*Diameter across face.*—65–75 mm.

B. Corolla of ray florets

*Color (general tonality from a distance of three meters).*—White.

*Color (upper and lower surfaces).*—155D.

C. Corolla of disc florets:

*Color (mature).*—Yellow with green center, variable in size dependent on stage of maturity.

*Color (immature).*—Green.

D. Reproductive organs

*Androecium.*—Present only in disc florets; numerous.

*Gynoecium.*—Present in both disc and ray florets; numerous.

PLANT

A. General Appearance:
*Height.*—75 cm.
B. Foliage:
*Color* (*upper surface*).—146B.
*Color* (*under surface*).—147C.

*Shape.*—Pinnately lobed.

I claim:

1. A new and distinct cultivar of Chrysanthemum plant named Topper, as described and illustrated, and parts thereof.

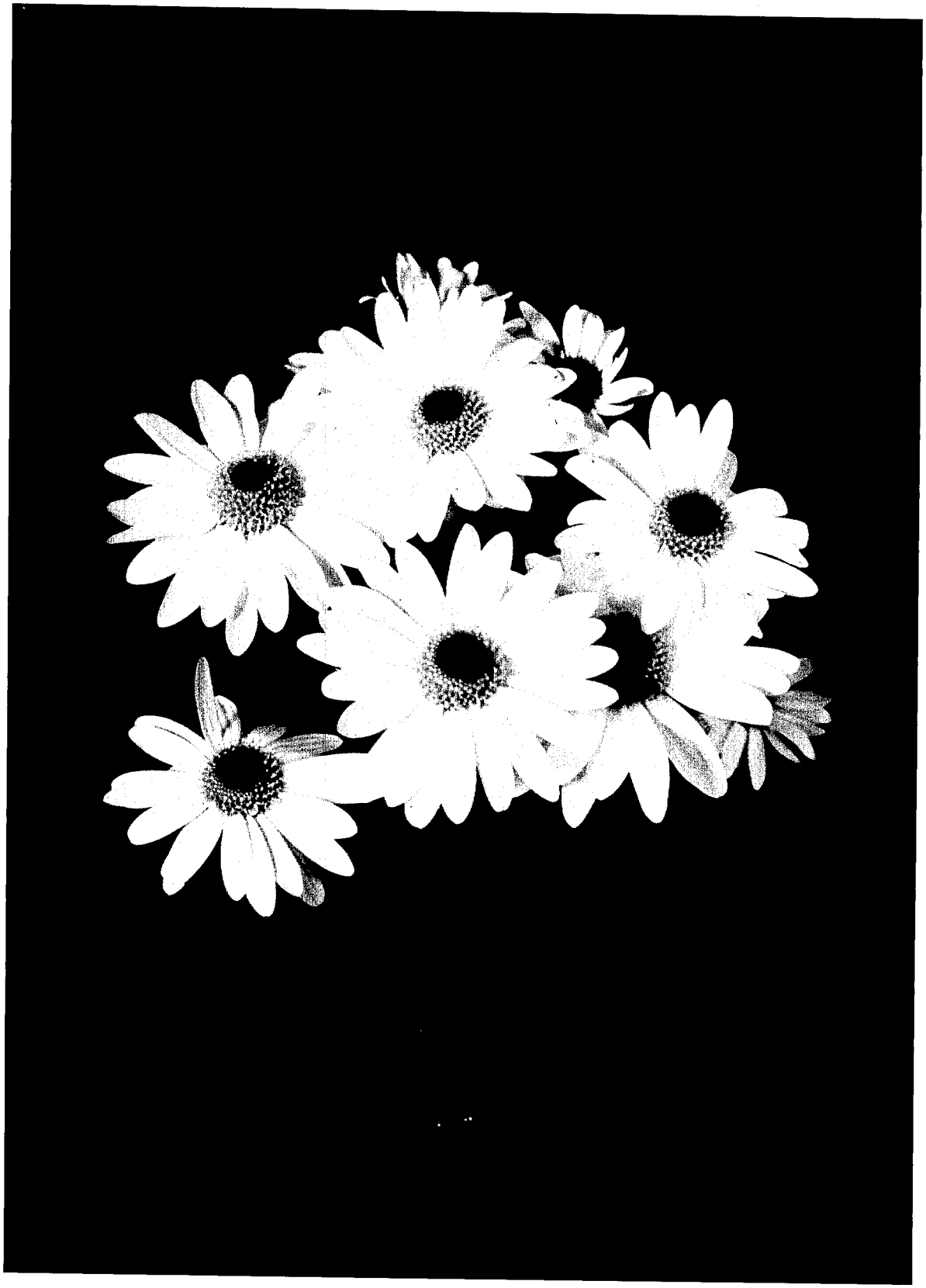

* * * * *